United States Patent [19]

Rogic et al.

[11] 4,393,215

[45] Jul. 12, 1983

[54] CLEAVAGE OF DIALKOXYKETOXIME

[75] Inventors: Milorad M. Rogic, Whippany; Bryce C. Oxenrider, Florham Park, both of N.J.

[73] Assignee: Allied Corporation, Morris Township, Morris County, N.J.

[21] Appl. No.: 280,754

[22] Filed: Jul. 6, 1981

[51] Int. Cl.$^3$ ............................................ C07D 271/08
[52] U.S. Cl. .............................. 548/125; 260/453 P; 260/453 AL; 260/465.4; 260/465.6; 548/122; 560/168; 560/231
[58] Field of Search ...................... 548/125; 260/465.4, 260/143, 464, 465.6; 560/168, 231; 564/258

[56] References Cited

U.S. PATENT DOCUMENTS 4,045,422 8/1977 Swerdloff et al. .................. 260/143
4,140,717 2/1979 Oxenrider et al. ............. 260/566 A

OTHER PUBLICATIONS

Klein et al.; Chem. Abs., vol. 90: 86809p (1979).
Oxenrider et al.; Chem. Abs., vol. 97: 5832k (1982).

*Primary Examiner*—Mary C. Lee
*Attorney, Agent, or Firm*—Alan M. Doernberg; Gerhard H. Fuchs

[57] ABSTRACT

Dialkoxyketoximes such as dimethoxycyclohexanone cleave with halogen and water under basic conditions to yield a series of products having an ester functionality and another functionality which is oximohalide, nitrile oxide or furoxan, depending upon the base strength and/or work-up conditions. Each of those products can be further reacted with sulfur dioxide to produce an adduct, from which an isocyanate is derived. Both the adduct and the isocyanate retain the ester functionality.

6 Claims, No Drawings

CLEAVAGE OF DIALKOXYKETOXIME

DESCRIPTION

BACKGROUND OF THE INVENTION

The present invention relates to the production of cleavage products from dialkoxyketoxime and especially to the production of nitrile oxides, furoxans and isocyanates from dialkoxyketoxime (with esters as by-products or additional functionalities) by reaction with a halogen and water under basic conditions.

Our U.S. Pat. No. 4,140,717 describes the halogenation of dialkoxyketoximes and especially alpha, alpha-di-alkoxycycloalkyl ketoximes in the presence of an acid catalyst to produce corresponding compounds with halogen on the beta position (the carbon adjacent to the carbon bonded to both alkoxies). No cleavage is involved in that reaction.

BRIEF DESCRIPTION OF THE INVENTION

The present invention includes a process in which a dialkoxyketoxime is reacted under basic conditions to produce cleavage products and is operable to produce nitrile oxides, furoxans and isocyanates from such a dialkylketoxime. If the starting material is an alpha,alpha-dialkoxycycloalkyl ketoxime, the products will also have ester functionalities remote from the nitrogen-containing functionalities.

Thus the present invention includes a process of cleaving a dialkoxyketoxime which comprises reacting in the liquid phase a dialkoxyketoxime of the formula

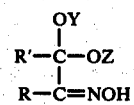

wherein Y and Z are each independently linear or branched alkyl and R and R' are each independently linear or branched alkyl or are together —(CH$_2$)$_n$— where n is an integer from 3 to 10, with a halogen selected from elemental chlorine and elemental bromine in the presence of a base and at least an equimolar amount of water under conditions forming a product selected from the group consisting of an oximohalide of the formula:

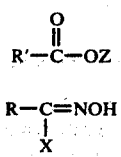

where R, R' and Z are as defined above and X is Cl or Br; a nitrile oxide of the formula:

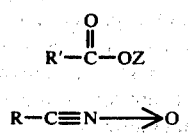

a furoxan of the formula:

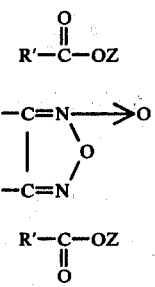

and mixtures thereof.

DETAILED DESCRIPTION OF THE INVENTION

The present invention includes reactions of dialkyloxyketoximes with a halogen and at least an equimolar amount of water. The oxime is of formula I:

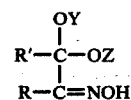

In formula I, R and R' can each be linear or branched alkyl of any length (e.g. 1–6 carbons), preferably alkyl of 1–3 carbons. Preferably R and R' are together —(CH$_2$)$_n$— where n is an integer of 3 to 10 carbons such that the oxime is a 2,2-dialkoxycycloalkanone oxime of 5–12 ring carbons (e.g. 2,2-dialkoxycyclopentanone oxime thru 2,2-dialkoxycyclododecanone oxime). Y and Z are both linear or branched alkyl of any length (e.g. 1–6 carbons), preferably alkyl of 1–3 carbons.

The suitable oximes include 2,2-dimethoxycyclopentanone oxime, 2,2-dimethoxycyclohexanone oxime, 2,2-diethoxycyclohexanone oxime, 2,-methoxy,2-pentoxycyclohexanone oxime, 2,2-dimethoxycyclooctanone oxime, 2,2-diethoxycyclodecanone oxime, 2,2-dimethoxycyclodecanone oxime, 3,3-dipropoxybuta-2-none oxime, 2,2-diethoxypenta-3-none oxime, 4,4-dimethoxyhexa-3-none oxime, 3,3-diethoxyhexa-2-none oxime, 2,2-dimethoxydeca-3-none oxime, and 5,5-dimethoxydodeca-4-none oxime. Cycloalkanone oxime derivatives (R and R' being —(CH$_2$)$_n$—) are preferred and cyclohexanone oxime derivatives (n being 4) are more preferred.

The halogen may be either elemental chlorine or elemental bromine, either in gaseous or liquid form, preferably at a stoichiometric or equimolar amount, or a slight excess, but less desirably at larger excesses or as a limiting reagent.

The reaction should occur in the liquid phase, either in neat oxime or in a solvent therefore such as a chlorinated hydrocarbon (e.g. dichloromethane). Water should be present in at least an amount equimolar to the limiting reagent (usually the oxime). Any temperature that permits liquid phase reaction is suitable, with at or near room temperature being preferred.

Any base sufficient in strength and quantity to neutralize byproduct hydrogen halide may be used. The strength of the base has an effect upon the product formed, with bases of base strength no greater than that of pyridine producing predominantly oximino halide of formula II:

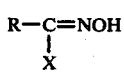

and stronger bases producing initially a nitrile oxide of formula III:

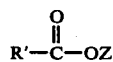

provided that sufficient strong base is present to neutralize both equivalents of hydrogen halide formed. It should be appreciated that when the oxime starting material is non-cyclic, the ester

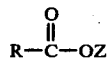

will be a separate product in both cases and not participate further. The nitrile oxide will be simply R—C≡N—>O, and the oximinohalide will be simply R—C(x)=NOH. If, however, the starting material is a cycloalkanone oxime derivative as is preferred, the ester will be at the opposite end of the —(CH$_2$)$_n$— chain from the oximinohalide or nitrile oxide functionality.

Either of the two initial products will dimerize reversibly over time to a furoxan of formula IV:

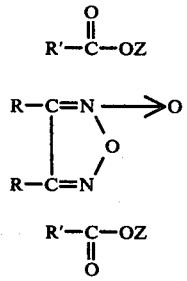

wherein R, R' and Z are as described above and, again, the two esters may be separate if R and R' are separately alkyl. The furoxan can be resplit into the nitrile oxide by heating. To form furoxan from the oximinohalide generally requires that the base still be present in amounts sufficient to neutralize hydrogen halide formed.

Any of the three products can be reacted with sulfur dioxide under mild conditions (e.g. room temperature) to form an adduct of formula V:

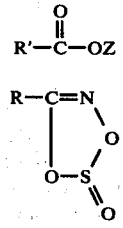

Thermal decomposition (e.g. heating between about 50 and about 150° C.) will yield the isocyanate of formula VI:

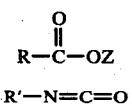

It should be appreciated that when R and R' are alkylene, formula VI represents a difunction esterisocyanate such as methyl-4-isocyanatovalerate (see Example 6).

The final product isocyanates are particularly useful as chain terminating agents in polyurethane systems since the isocyanate functionality is the only one which will react under urethane-forming conditions. Subsequently, the ester functionality can be unblocked by known saponification methods, and the free acid functionalities either used for grafting other groups or as chelating sites.

In particular, when R and R' are together alkylene, certain of the products represent novel materials. In particular, the isocyanates of formula VII are especially useful:

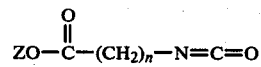

with Z being alkyl and n being an integer from 3 to 10, preferably 4.

EXAMPLE 1

To a solution of 2,2-dimethoxycyclohexanone oxime (4.32 g, 25 mmol), in 50 mL of anhydrous methanol, anhydrous disodium phosphate (11.0 g, 77 mmol) and water (0.5 g, 28 mmol) were added. The mixture was treated with chlorine (1.8 g, 25 mmol) at 25° C. over a fifteen minute period. After stirring for 30 min, the solids were filtered off, and most of the solvent removed by evaporation. Methylene chloride (50 mL) was added, filtered and evaporated at room temperature. There was obtained 4.8 g (94% yield) of a red-brown liquid, shown by both proton and carbon-13 NMR to be 4-methoxycarbonylpentanooximino chloride.

EXAMPLE 2

Example 1 was repeated using 2,2-dimethyoxycyclooctanone oxime (5.02 g, 25 mmol). The product was shown by NMR to be 6-methoxycarbonylheptanooximino chloride.

EXAMPLE 3

A reaction mixture of 2,2-dimethoxycyclohexanone oxime (8.65 g, 50 mmol), sodium bicarbonate (12.6 g, 150 mmol), methylene chloride (25 mL), and water (25 mL), was stirred in an ice-water bath. Chlorine (3.5 g, 50 mmol) was introduced over 30 min, and then stirred for 1.5 hr. Methylene chloride layer was separated, dried, and evaporated at room temperature. There was obtained 7.2 g (93% yield) of a yellow liquid which according to IR analysis was a mixture of the nitrile oxide (2300 cm$^{-1}$) and furoxan (1603 cm$^{-1}$). On standing overnight at room temperature the infra-red band at 2300 cm$^{-1}$ disappeared and the band at 1603 cm$^{-1}$ strengthened indicating dimerization of the nitrile oxide into a furoxan. Column chromotography on neutral alumina gave the furoxan, whose structure was confirmed by NMR and mass spectroscopy.

EXAMPLE 4

Addition of bromine (2 g, 25 mmol) to a well stirred mixture of 2,2-dimethoxycyclohexanone oxime (4.32 g, 25 mmol), disodium phosphate (10.65 g, 75 mmol) in 40 mL of methylene chloride, and 40 mL of water at room temperature, followed by separation of methylene chloride layer and drying, gave a crude nitrile oxide in solution. Without isolation, sulfur dioxide (1.8 g, 28 mmol) was introduced, stirred for 15 min and then evaporated. There was obtained 5.0 g (90% yield) of its sulfur dioxide adduct as a slightly tan-colored liquid, whose structure was confirmed by both proton and carbon-13 NMR. The same product was also obtained from the reaction of 4-methoxycarbonylpentanooximinochloride (from Example 1) with a molar equivalent of pyridine and sulfur dioxide in methylene chloride solution.

EXAMPLE 5

In a reaction similar to Example 4, 2,2-dimethoxycyclooctanone oxime (5.02 g, 25 mmol) was converted to its sulfur dioxide complex (4.5 g, 72.6% yield) and its structure was confirmed by both proton and carbon-13 NMR.

EXAMPLE 6

The sulfur dioxide complex of 4-methoxycarbonylpentanonitrile oxide (from Example 4) was refluxed in cyclohexane until sulfur dioxide evolution ceased. Evaporation of cyclohexane gave about 60% yield of methyl-4-isocyanatovalerate bp 50° C. (0.4 mm) whose structure was confirmed by proton NMR and by derivatization with aniline.

EXAMPLE 7

The sulfur dioxide complex of Example 5 was refluxed until sulfur dioxide evolution ceased. Evaporation of cyclohexane gave 6-isocyanatoheptanoic acid methyl ester, whose structure was confirmed by both proton and carbon-13 NMR.

EXAMPLE 8

A solution of 2,2-dimethoxycyclohexanone oxime (8.65 g, 50 mmol) in dry methylene chloride (50 mL) and pyridine (3.95 g, 50 mmol) was treated with chlorine (3.55 g, 50 mmol) over 1.2 h at 15° C. After stirring for 2 h at room temperature, the solution was washed three times with equal volumes of cold water and evaporated. There was obtained 9.8 g of yellow liquid which, according to mass spectrum was a mixture of 5-methoxycarbonylvaleronitrile, 5-methoxycarbonylvalerylnitrile oxide, 4-methoxycarbonylpentanooximinochloride, and 4,5-bis(methoxycarbonylbutyl)-furoxan and the corresponding furazan.

What is claimed:

1. A process of cleaving a dialkoxyketoxime which comprises reacting in the liquid phase a dialkoxyketoxime of the formula:

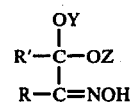

wherein Y and Z are each independently linear or branched alkyl and R and R' are each independently linear or branched alkyl or are together —$(CH_2)_n$— where n is an integer from 3 to 10, with a halogen selected from elemental chlorine and elemental bromine in the presence of a base and at least an equimolar amount of water under conditions forming a product selected from the group consisting of an oximinohalide of the formula:

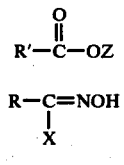

where R, R' and Z' are as defined above and X is Cl or Br; a nitrile oxide of the formula:

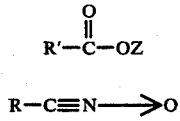

a furoxan of the formula:

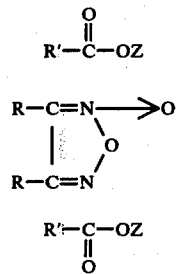

and mixtures thereof.
2. The process of claim 1 wherein said base has a base strength no greater than that of pyridine and the predominant product is said oximinohalide.
3. The process of claim 1 or 2 wherein R and R' are together —$(CH_2)_n$—.
4. The process of claim 3 wherein n is 4.
5. The process of claim 2 wherein said base is disodium hydrogen phosphate.
6. The process of claim 1 wherein said halogen is elemental chlorine.

* * * * *